United States Patent
Okada et al.

(10) Patent No.: US 9,713,515 B2
(45) Date of Patent: Jul. 25, 2017

(54) SHELL PLATE FOR ARTIFICIAL TEETH WITH ARRANGEMENT ASSISTING FUNCTION

(71) Applicant: KABUSHIKI KAISHA SHOFU, Kyoto (JP)

(72) Inventors: Hisashi Okada, Kyoto (JP); Noriyuki Negoro, Kyoto (JP); Kunihiro Fujii, Kyoto (JP); Hirokazu Sato, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 356 days.

(21) Appl. No.: 14/272,768

(22) Filed: May 8, 2014

(65) Prior Publication Data
US 2014/0242549 A1 Aug. 28, 2014

Related U.S. Application Data

(63) Continuation of application No. 12/733,046, filed as application No. PCT/JP2007/065529 on Aug. 8, 2007.

(51) Int. Cl.
| | |
|---|---|
| *A61C 19/10* | (2006.01) |
| *A61C 13/01* | (2006.01) |
| *A61C 13/34* | (2006.01) |

(52) U.S. Cl.
CPC .............. *A61C 19/10* (2013.01); *A61C 13/01* (2013.01); *A61C 13/34* (2013.01)

(58) Field of Classification Search
CPC .......... A61C 19/10; A61C 13/01; A61C 13/34
See application file for complete search history.

(56) References Cited

U.S. PATENT DOCUMENTS

| | | | | |
|---|---|---|---|---|
| 1,518,075 | A | 12/1924 | Kesling | |
| 2,383,027 | A * | 8/1945 | Tryfus | A61C 19/10 |
| | | | | 433/26 |
| 2,554,044 | A * | 5/1951 | McNeill | A61C 19/10 |
| | | | | 206/83 |

(Continued)

FOREIGN PATENT DOCUMENTS

| | | |
|---|---|---|
| DE | 1 098 670 | 5/1959 |
| DE | 39 10 393 | 10/1990 |

(Continued)

OTHER PUBLICATIONS

Japanese Office Action issued Jun. 26, 2012 in corresponding Japanese Application No. 2009-526296.

(Continued)

*Primary Examiner* — Cris L Rodriguez
*Assistant Examiner* — Hao D Mai
(74) *Attorney, Agent, or Firm* — Wenderoth, Lind & Ponack, L.L.P.

(57) ABSTRACT

An artificial teeth packaging container includes an artificial teeth accommodating portion for fixing a plurality of continuously arranged artificial teeth detachably, and holding an arrangement position relation with an adjacent artificial teeth and an arrangement position relation with an upper or lower artificial molar teeth, in which the artificial teeth accommodating portion covers the plurality of artificial teeth from an occlusal plane in a state exposed around a cervical portion.

8 Claims, 8 Drawing Sheets

(56) References Cited

U.S. PATENT DOCUMENTS

| | | | |
|---|---|---|---|
| 2,889,598 A * | 6/1959 | Lundquist | A61C 13/26 |
| | | | 164/246 |
| 3,111,760 A | 11/1963 | Semmelman et al. | |
| 4,299,573 A | 11/1981 | Ricci | |
| 4,401,616 A | 8/1983 | Wagner | |
| D273,893 S * | 5/1984 | Weitzman | D24/181 |
| 5,890,895 A | 4/1999 | Tucker | |
| 6,182,820 B1 | 2/2001 | Rathbauer | |
| 6,364,665 B1 | 4/2002 | Trettenero | |
| 6,379,147 B1 | 4/2002 | Georgakis et al. | |
| 6,415,916 B1 * | 7/2002 | Rini | A61C 19/10 |
| | | | 206/459.5 |
| 6,447,296 B2 | 9/2002 | Worthington | |
| 6,652,276 B2 | 11/2003 | Fischer et al. | |
| 6,848,905 B2 | 2/2005 | Jacobs et al. | |
| D509,000 S * | 8/2005 | Barnes | D24/176 |
| 6,945,778 B2 | 9/2005 | Jacobs et al. | |
| 7,090,073 B2 * | 8/2006 | Barnes | A61C 19/10 |
| | | | 206/368 |
| 7,648,360 B2 | 1/2010 | Kuo | |
| D705,540 S * | 5/2014 | Phillips | D3/273 |
| 2001/0036618 A1 | 11/2001 | Worthington | |
| 2004/0014007 A1 | 1/2004 | Lee et al. | |
| 2004/0086831 A1 | 5/2004 | Lai | |
| 2004/0161726 A1 | 8/2004 | Saito et al. | |
| 2005/0042577 A1 | 2/2005 | Kvitrud et al. | |
| 2005/0244770 A1 | 11/2005 | Worthington | |
| 2006/0210945 A1 | 9/2006 | Savic et al. | |
| 2006/0263749 A1 | 11/2006 | Koide | |
| 2009/0050161 A1 | 2/2009 | Burdumy | |

FOREIGN PATENT DOCUMENTS

| | | |
|---|---|---|
| DE | 10 2005 013 459 | 10/2006 |
| DE | 20 2006 015 388 | 4/2007 |
| JP | 8-280712 | 10/1996 |
| JP | 2000-237213 | 9/2000 |
| JP | 2001-070322 | 3/2001 |
| JP | 2001-137262 | 5/2001 |
| JP | 2002-315764 | 10/2002 |
| JP | 2003-310645 | 11/2003 |
| JP | 2004/096077 | 11/2004 |

OTHER PUBLICATIONS

Chinese Office Action issued Apr. 16, 2012 in corresponding Chinese Application No. 200780100962.2.

* cited by examiner

SHELL PLATE FOR ARTIFICIAL TEETH WITH ARRANGEMENT ASSISTING FUNCTION

The present application is a continuation application of U.S. patent application Ser. No. 12/733,046, filed Feb. 4, 2010, which is a national stage entry of PCT/JP2007/065529 filed Aug. 8, 2007. The entirety of U.S. patent application Ser. No. 12/733,046 is hereby incorporated by reference. Application Ser. No. 12/733,046 was published as U.S. Pre-grant Publication Number 2010/0136505 on Jun. 3, 2010, and the entirety of this publication is hereby incorporated by reference.

BACKGROUND OF THE INVENTION

Technical Field

The present invention relates to an artificial teeth packaging container used for the purpose of conveying and storing the artificial teeth when manufacturing a denture in dental treatment.

Description of the Related Art

Existing artificial teeth are disposed on a protuberance formed on a wax rim when manufacturing a denture by using an articulator, and the arrangement is adjusted by matching with a state of occlusion of individual patients. The artificial teeth usually include twelve artificial teeth for the upper jaw and the lower jaw corresponding to right and left central incisors, lateral incisors, and canine teeth, and sixteen artificial teeth for the upper jaw and the lower jaw corresponding to first premolars, second premolars, first molars, and second molars for right and left. Usually when selling the artificial teeth, six anterior teeth for the upper jaw and the lower jaw, or eight artificial molar teeth for the upper jaw and the lower jaw are arranged in a row, and fixed on a resin-made seat plate by adhesive wax or the like (see, for example, Japanese Patent Application Laid-Open No. 2000-237213 and Japanese Patent Application Laid-Open No. 2002-315764). In order to inform a dentist or a dental technician of necessary information such as a color and a shape of the artificial teeth and manufacturer's name, the seat plate has a display space positioned above or beneath an accommodating portion of the artificial teeth.

Japanese Patent Application Laid-Open No. 2003-310645 discloses a seat plate attached to artificial teeth so that the shape and color may be selected easily. However, in the configuration shown in Japanese Patent Application Laid-Open No. 2000-237213, Japanese Patent Application Laid-Open No. 2002-315764 and Japanese Patent Application Laid-Open No. 2003-310645, since an upper, lower, right and left positional relation of the artificial teeth is not clear, when arranging the artificial teeth, occlusion adjustment work is difficult depending on the artificial teeth to be arranged, and a denture not suited sufficiently to an occlusal state of a patient may be manufactured. Besides, in such seat plate, in the manufacturing process, the artificial teeth may be adhered by mistake to a different position than a position specified on the seat plate. Further, when the artificial teeth are used, the sorting and discarding of the seat plate may be complicated.

Different from the seat plate in Japanese Patent Application Laid-Open No. 2000-237213, Japanese Patent Application Laid-Open No. 2002-315764 and Japanese Patent Application Laid-Open No. 2003-310645, in order to arrange easily in a prosthetic positional relation, Japanese Patent Application Laid-Open No. 2001-137262 discloses upper and lower connected artificial teeth of artificial teeth coupled to a maintenance holder with upper and lower artificial teeth connected detachably. However, in this configuration, separation work of the artificial teeth and the maintenance holder is needed after arrangement, or when cutting off the connected portion, nippers or similar tools may be needed, and the operation in the arrangement process may be more complicated.

SUMMARY OF THE INVENTION

It is hence an object of the invention to enhance a working efficiency in arrangement process, curtail a use of materials, stabilize an efficiency in the manufacturing process, and suppress the environmental load by discarding, by adding an arrangement assisting function to a packaging material mainly used for the purpose of storing and conveying the artificial teeth.

In order to solve the above-mentioned problems, the present invention provides an artificial teeth packaging container including: an artificial teeth accommodating portion for fixing a plurality of continuously arranged artificial teeth detachably, and holding an arrangement position relation with the adjacent artificial teeth and an arrangement position relation with an upper or lower artificial molar teeth, wherein the artificial teeth accommodating portion covers the plurality of artificial teeth from an occlusal plane in a state exposed around a cervical portion.

Preferably, an artificial teeth accommodating portion includes an artificial first premolar tooth accommodating portion, an artificial second premolar tooth accommodating portion, an artificial first molar tooth accommodating portion, and an artificial second molar tooth accommodating portion, and wherein a peripheral wall at the artificial first premolar tooth accommodating portion of the artificial accommodating portion is provided with a positioning slit for adjusting an arrangement position relation between artificial first premolar tooth and artificial canine tooth.

Preferably, a plane plate portion disposed in parallel to a virtual occlusal plane is provided in a peripheral wall of a lingual side surface contact side of the artificial teeth accommodating portion.

Preferably, the artificial teeth packaging container is made of a resin material of about 0.2 mm to 2 mm in thickness, and is selected from polyvinyl chloride, polystyrene, polyethylene terephthalate, polypropylene, or amorphous polyethylene terephthalate.

Preferably, the peripheral wall of the artificial teeth accommodating portion is extended from a maximum prominent portion of the plurality of artificial teeth toward a cervical portion side, and contacts along the plurality of artificial teeth.

Preferably, a through-hole for injection of adhesive agent is provided in an occlusal plane contact side wall portion of the artificial teeth accommodating portion, in the vicinity of a center of each occlusal plane with the plurality of artificial teeth.

Preferably, the plurality of artificial teeth are pressed and fixed in the peripheral wall of the artificial teeth accommodating portion.

An accommodating state of artificial teeth in an artificial teeth packaging container of the invention is preferably a state where the artificial teeth are accommodated in an arrangement state. More preferably, upon manufacturing the denture, when the artificial teeth contained in the artificial teeth packaging container are waxed, an artificial arrangement should be formed on the denture, so that a plurality of artificial teeth may be arranged in batch while maintaining an arrangement position relation with the adjacent artificial teeth and an arrangement position with upper or lower artificial teeth. Therefore, the arrangement work of the artificial teeth may be easier and more efficient. As compared with the conventional seat plate, since a package structure is simple, and manufacturing materials may be saved, and the efficiency in the manufacturing process may be stabilized. Moreover, since fixing of the artificial teeth is free from effects of temperature changes during the conveying or storing process, and separation or loss of the artificial teeth may be prevented.

BRIEF DESCRIPTION OF THE DRAWINGS

FIG. 1(a) is a perspective view showing a method of fixing an artificial teeth packaging container in an embodiment of the invention in lower-jaw left artificial molar teeth, and (b) is a perspective view of the artificial teeth packaging container of (a) in a state of fixing of the lower-jaw left artificial molar teeth.

FIG. 13(a) is a right side view showing a modified example of the artificial teeth packaging container in an embodiment of the invention provided with a gripping plate for assisting separation, and (b) is a magnified sectional view along line B-B of the artificial teeth packaging container in (a), showing a state of the artificial first premolar tooth fixed in the artificial first premolar tooth accommodating portion.

DETAILED DESCRIPTION OF THE INVENTION

The invention is described below while referring to the accompanying drawings.

FIG. 1 to FIG. 11 show an artificial teeth packaging container 1 according to a preferred embodiment of the invention for packaging artificial teeth. Herein, the "artificial teeth" refer to teeth of existing products used when manufacturing a denture as an artificial human organ, and various types and shapes are available depending on the variety, color, and form, and when the artificial teeth are classified roughly, ceramic teeth made of porcelain materials, and resin teeth made of resin materials are used. The artificial teeth are usually sold individually as each set of six upper artificial anterior teeth, six lower artificial anterior teeth, eight upper artificial molar teeth, and eight lower artificial molar teeth. The "occlusal plane" refers to a plane defined by including a middle point of mesial corners of lower-jaw right and left lateral incisor cutting edges, and distal buccal cusps of right and left second molar teeth. The "virtual occlusal plane" refers to a plane determined by utilizing the Camper's plane formed by either right or left nasal alar lower edge and both tragus upper edges, and it is the reference for setting the occlusal plane.

The artificial teeth packaging container 1 includes an elastic resin material, and is designed to package a plurality of artificial teeth arranged sequentially in an arbitrary combination as shown in FIG. 1 to FIG. 9, and in the embodiment, an example is explained about a container for packaging of four lower-jaw left artificial molar teeth 2 (i.e., a set of non-natural molar teeth each corresponding to a respective one of a set of natural molar teeth found in a human jaw) including a lower-jaw left artificial first premolar tooth 3, a lower-jaw left artificial second premolar tooth 4, a lower-jaw left artificial first molar tooth 5, a lower-jaw left artificial second molar tooth 6.

Figure 1:
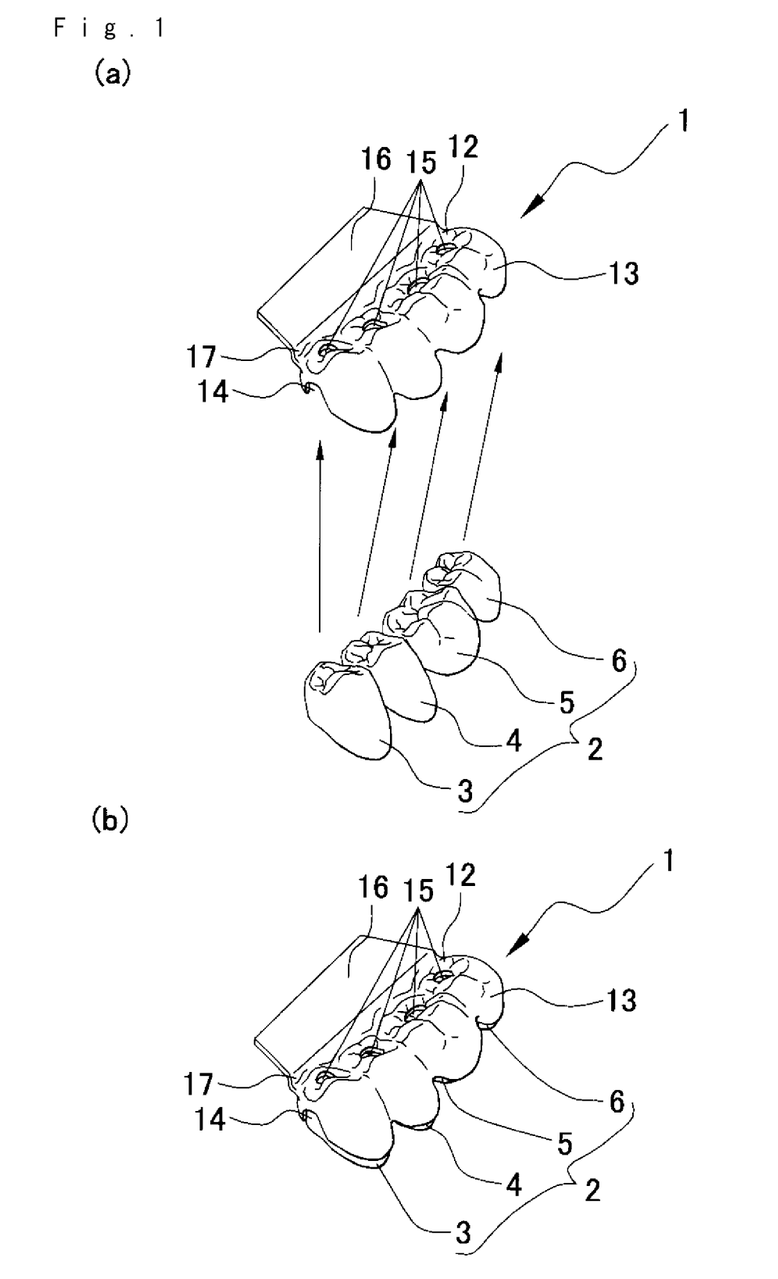
Figure 2:
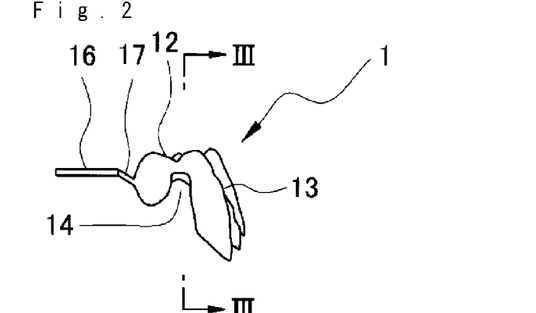
FIG. 2 is a front view of the artificial teeth packaging container shown in FIG. 1.
Figure 3:
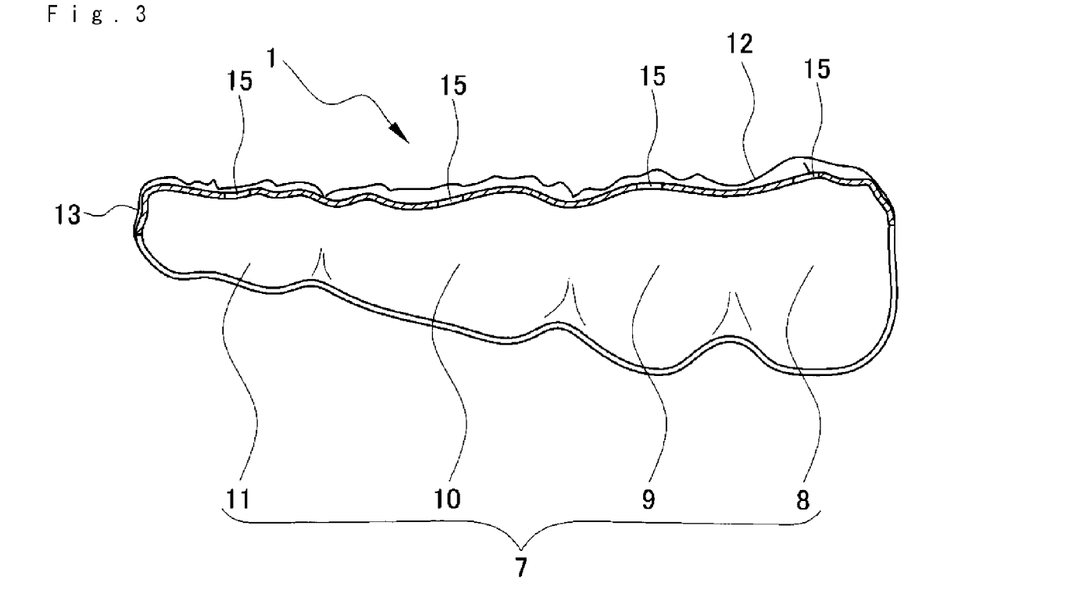
FIG. 3 is a sectional view along line III-III of the artificial teeth packaging container shown in FIG. 2.
Figure 4:
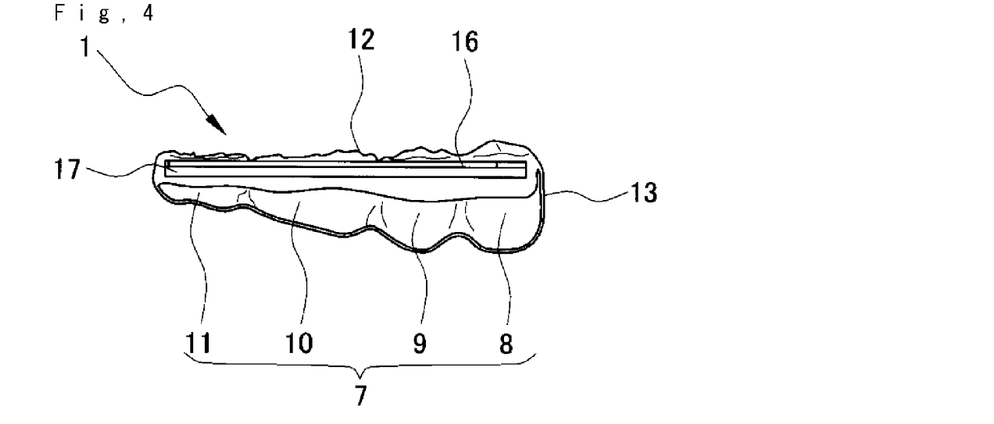
FIG. 4 is a left side view of the artificial teeth packaging container shown in FIG. 1.
Figure 5:
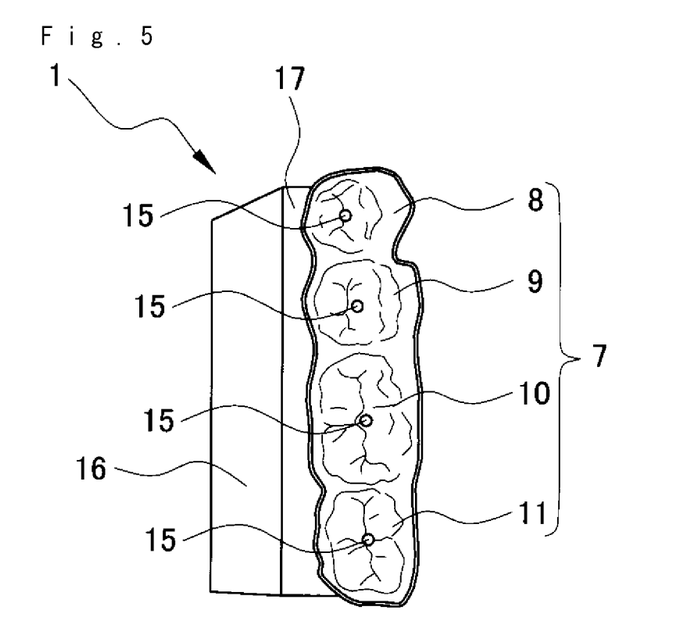
FIG. 5 is a bottom side view of the artificial teeth packaging container shown in FIG. 1.
Figure 6:
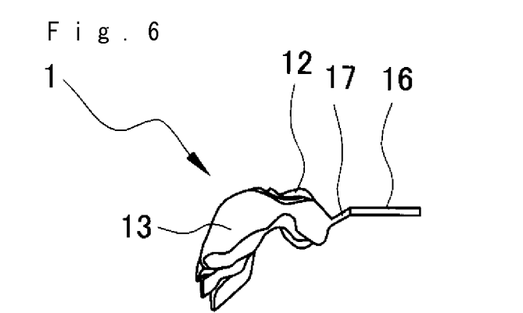
FIG. 6 back side view of the artificial teeth packaging container shown in FIG. 1.
Figure 7:
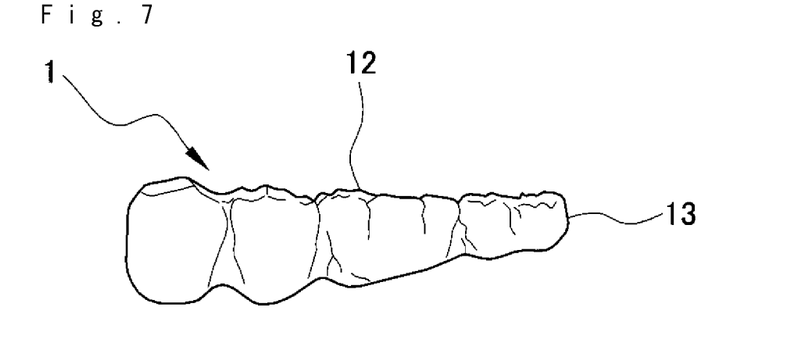
FIG. 7 is a right side view of the artificial teeth packaging container shown in FIG. 1.
Figure 8:
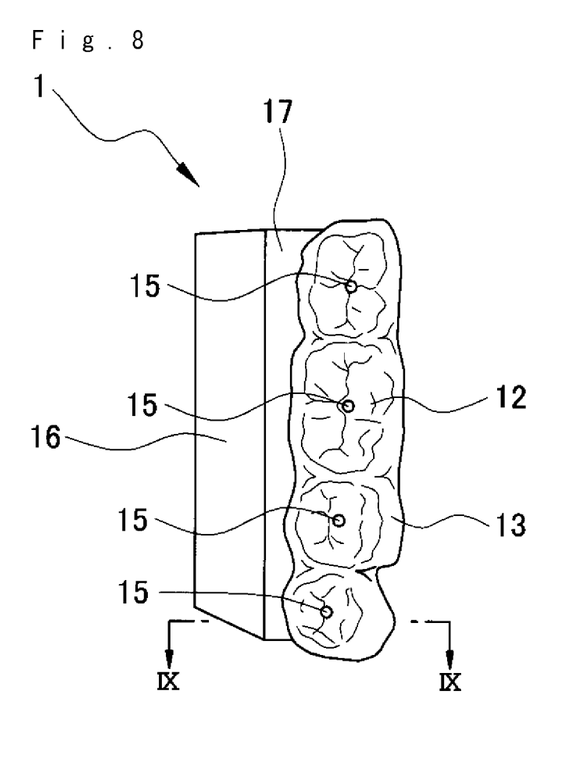
FIG. 8 is a plan view of the artificial teeth packaging container shown in FIG. 1.
Figure 9:
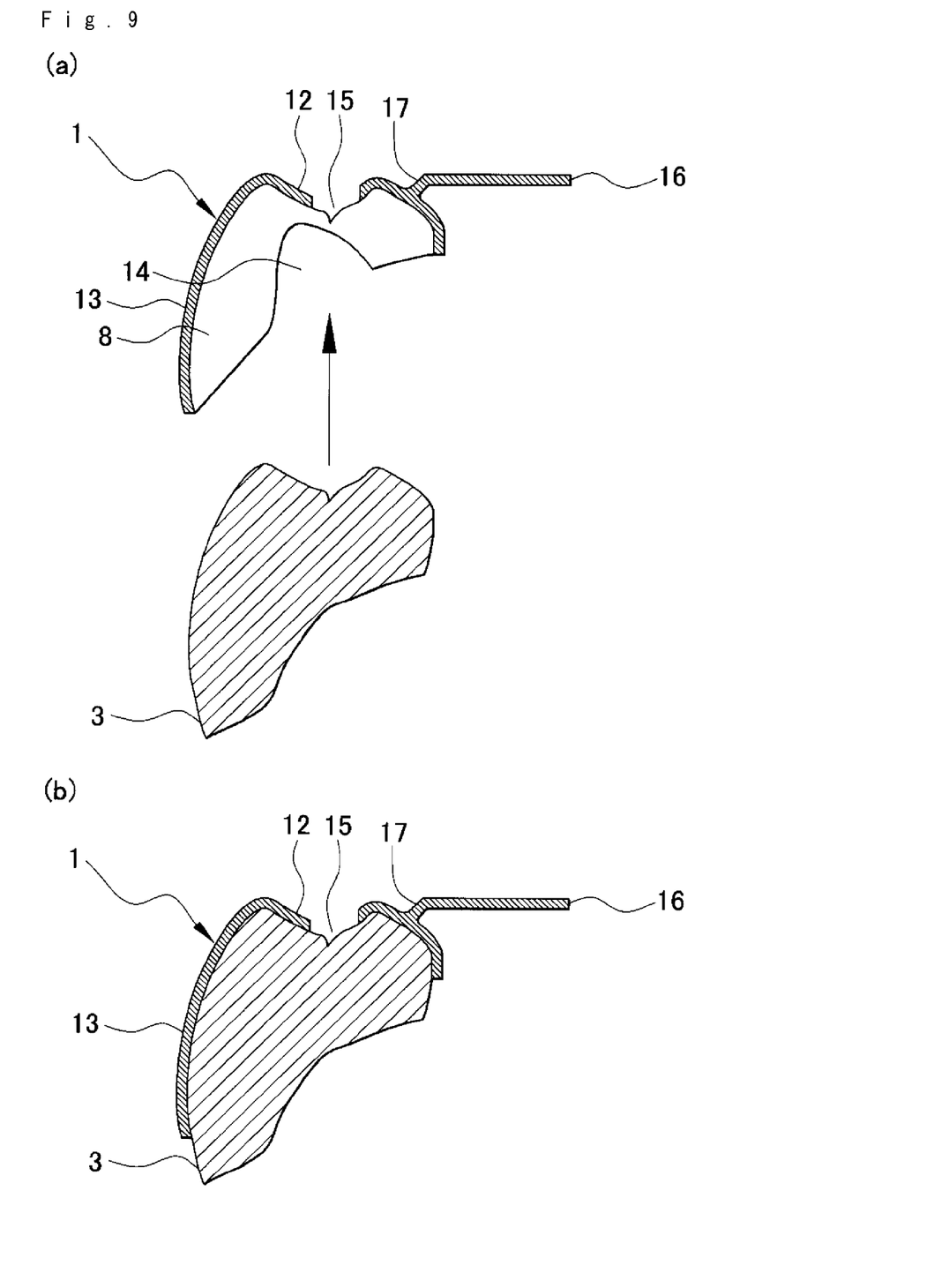
FIG. 9 is a sectional view along line IX-IX of the artificial teeth packaging container shown in FIG. 7, showing a method of fixing the artificial first premolar tooth to the artificial first premolar tooth accommodating portion.

The artificial teeth packaging container 1 includes, as shown in FIG. 3 to FIG. 5, an artificial teeth accommodating portion 7 for accommodating four lower-jaw left artificial molar teeth 2 formed in a specified shape. The artificial teeth accommodating portion 7 includes an artificial first premolar tooth accommodating portion 8 for accommodating and fixing a lower-jaw left artificial first premolar tooth 3, an artificial second premolar tooth accommodating portion 9 for accommodating and fixing a lower-jaw left artificial second premolar tooth 4, an artificial first molar tooth accommodating portion 10 for accommodating and fixing a lower-jaw left artificial first molar tooth 5, and an artificial second molar tooth accommodating portion 11 for accommodating and fixing a lower-jaw left artificial second molar tooth 6. In other words, the artificial teeth 2 are arranged in the artificial teeth accommodating portion 7 so as to have a prosthetic positional relationship in which alignment of the artificial teeth 2 is based on a set of natural teeth found in a human jaw. The artificial teeth accommodating portion 7, as shown in FIG. 1 to FIG. 4, includes an occlusal surface contact side wall portion 12 contacting with an occlusal plane of the lower-jaw left artificial molar teeth 2, and a peripheral wall 13 contacting with a side surface of the lower-jaw left artificial molar teeth 2. Inner surfaces of the occlusal surface contact side wall portion 12 and the peripheral wall 13 of the artificial teeth accommodating portion 7 are, as shown in FIG. 3, formed in a shape corresponding to the four lower-jaw left artificial molar teeth 2 arranged continuously in the order of the lower-jaw left artificial first premolar tooth 3, the lower-jaw left artificial second premolar tooth 4, the lower-jaw left artificial first molar tooth 5, the lower-jaw left artificial second molar tooth 6. Meanwhile, the inner surfaces of the occlusal surface contact side wall portion 12 and the peripheral wall 13 of the artificial teeth accommodating portion 7 are formed in a shape corresponding to an arrangement position relation with the adjacent artificial teeth and an arrangement position relation with the upper artificial molar teeth above corresponding to the lower-jaw left artificial molar teeth. The artificial teeth accommodating portion 7 covers the artificial molar teeth 3 to 6, from the occlusal plane with a periphery of a cervical portion exposed. The artificial teeth accommodating portion 7 includes a slit 14. The slit 14 is formed in the peripheral wall at the artificial first premolar tooth accommodating portion 8 side as shown in FIG. 2 and FIG. 9. The slit 14 is formed in a shape corresponding to the lower-jaw left artificial canine tooth 24 arranged adjacently to the lower-jaw left artificial first premolar tooth 3 as shown in FIG. 1, FIG. 2, and FIG. 9, and is extended toward the occlusal plane contact side wall portion 12. An inner side of a buccal surface connection side of the peripheral wall 13 of the artificial teeth packaging container 1 is extended, as shown in FIG. 9, from a maximum prominent portion of the lower-jaw left artificial molar teeth 3 to 6 toward a cervical portion side, and contacts with a buccal side of the lower-jaw left artificial molar teeth 3 to 6. The artificial teeth packaging container 1 has a through-hole 15 for injection of adhesive agent. The through-hole 15 for injection of adhesive agent is formed in a circular shape of 1 mm to 2 mm in diameter, and is formed in the occlusal plane contact side wall portion 12 of the artificial teeth accommodating portion 7. The through-hole 15 for injection of adhesive agent is positioned in the vicinity of the center of the occlusal plane of the artificial molar teeth 3 to 6 fixed to the artificial teeth accommodating portion 7.

Figure 12:
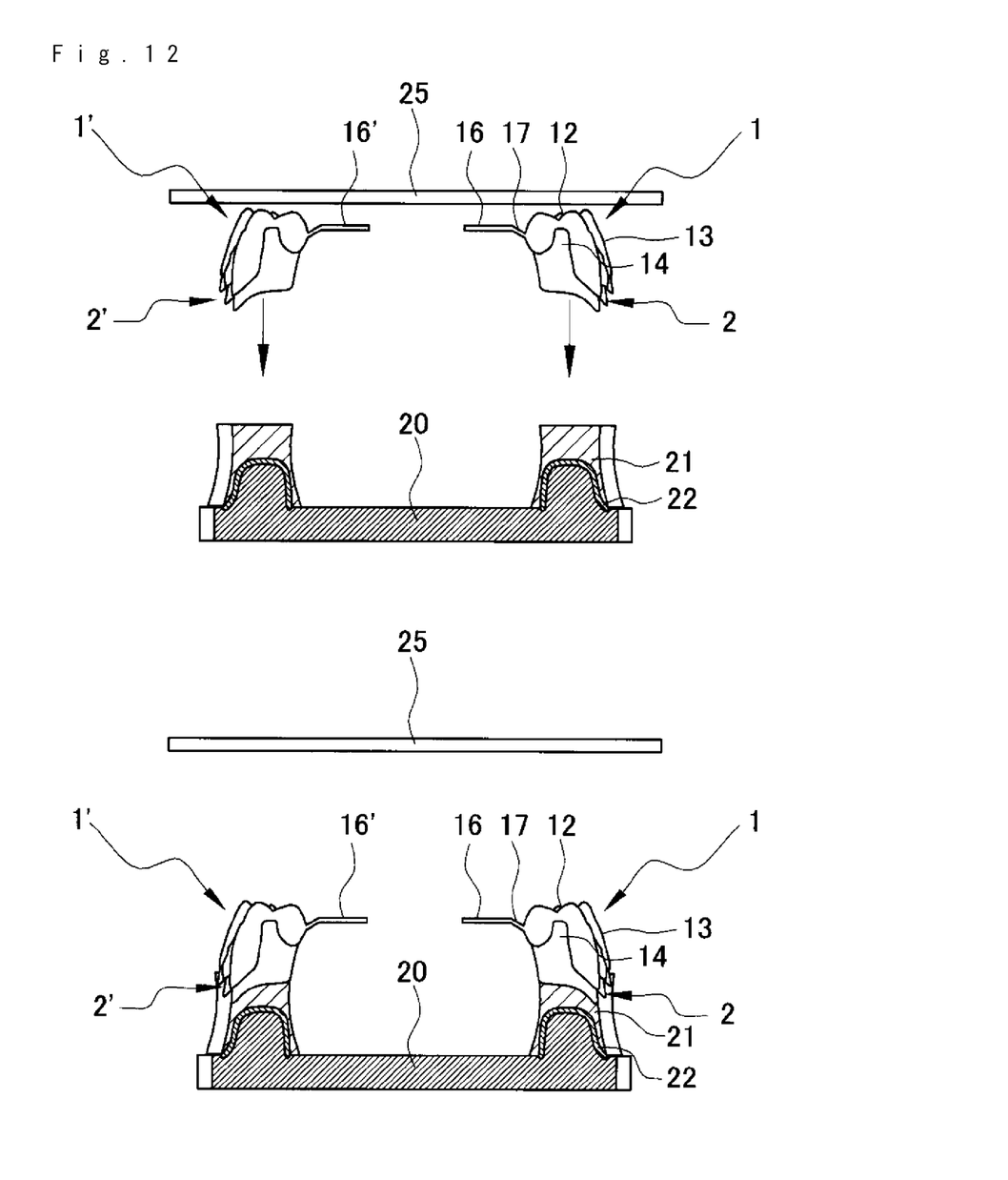
FIG. 12 is an explanatory diagram showing a method of arranging right and left lower artificial molar teeth in the wax rim by using the artificial teeth packaging container shown in FIG. 1.

The artificial teeth packaging container 1 includes a plane plate portion 16 disposed in parallel to a virtual occlusal plan. The plane plate portion 16 is coupled to an outer wall surface of a lingual surface contact side of the peripheral wall 13 by way of a connector 17, and is extended substantially perpendicularly to the outer wall surface of the lingual surface contact side of the peripheral wall 13 as shown in FIG. 12. The plane plate portion 16 displays necessary items such as a shape and a color of four lower-jaw left artificial molar teeth 3 to 6, and the manufacturer's name.

The artificial teeth packaging container 1 is preferably made of a thermo-curable material, being configured as a transparent container, and is manufactured by using a re-usable and elastic resin material of about 0.2 mm to 2.0 mm in thickness, such as polyvinyl chloride (PVC), polystyrene (PS), polyethylene terephthalate (PET), polypropylene (PP), or amorphous polyethylene terephthalate (A-PET). The artificial teeth packaging container 1 is formed by using a known method such as pressure air forming method of pressing a heated material film to a die.

The action of the embodiment is explained by referring to a case of packaging the lower-jaw left artificial molar teeth 2 by the artificial teeth packaging container 1.

When packaging the lower-jaw left artificial molar teeth 2 by using the artificial teeth packaging container 1 of the embodiment, as shown in FIG. 1 and FIG. 9, four lower-jaw left artificial molar teeth 3 to 6 are pushed and inserted into the corresponding artificial teeth accommodating portions 8 to 11. As a result, the artificial teeth packaging container 1 fixes the lower-jaw left artificial molar teeth 3 to 6 detachably into the corresponding artificial teeth accommodating portions 8 to 11. In the artificial teeth packaging container 1, hence, inner surfaces of a buccal side surface contact side of the peripheral wall 13 contact with each other by surpassing the maximum prominent portion of the lower-jaw left artificial molar teeth 3 to 6. As far as the peripheral wall 13 of a buccal side surface contact side of the artificial teeth packaging container 1 is not elastically deformed in the outside direction, the lower-jaw left artificial molar teeth 3 to 6 are limited in the motion of the lower-jaw left artificial molar teeth 3 to 6 by the maximum prominent portion, and are not dropped out of the artificial teeth accommodating part 7.

In this manner, inner surfaces of the artificial molar teeth accommodating portions 8 to 11 are formed in a shape corresponding to the four lower-jaw left artificial molar teeth 2, and are also formed in a shape corresponding to an arrangement position relation with the adjacent artificial teeth and an arrangement position relation with the upper artificial molar teeth above the corresponding to lower-jaw left artificial molar teeth 2, and therefore when the lower-jaw left artificial molar teeth 3 to 6 are fixed in the corresponding artificial molar teeth accommodating portions 8 to 11, the artificial teeth packaging container 1 maintains the arrangement position relation with the adjacent artificial teeth and the arrangement position relation with the upper artificial molar teeth above. The lower-jaw left artificial molar teeth 3 to 6 are fixed in the corresponding artificial molar teeth accommodating portions 8 to 11 by using a maximum prominent portion, and are free from effects of temperature changes in the conveying and storing process, and any one of the lower-jaw left artificial molar teeth 3 to 6 will not be dropped or lost from the artificial teeth packaging container 1.

If the maximum prominent portion is lost by cutting adjustment of artificial teeth, wax or other adhesive agent is injected from the through-hole 15 for injection of adhesive agent, and the lower-jaw left artificial molar teeth 3 to 6 are fixed in the artificial teeth accommodating portion 7.

A following explanation is about manufacturing work of a denture by using the lower-jaw left artificial molar teeth packaged by the artificial teeth packaging container 1 of the embodiment.

Figure 10:
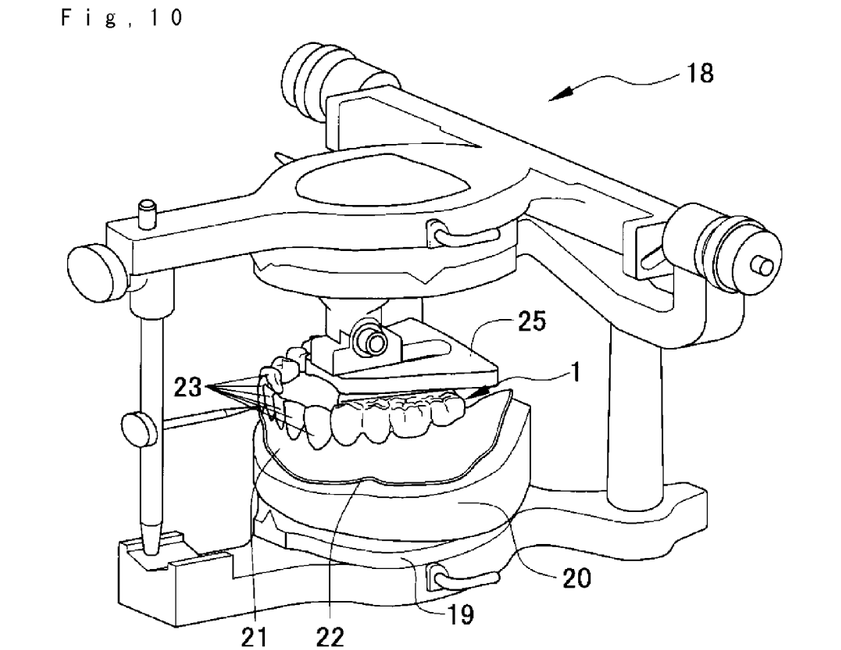
FIG. 10 is a perspective view of an articulator for adjusting an occlusal state of the artificial teeth.
Figure 11:
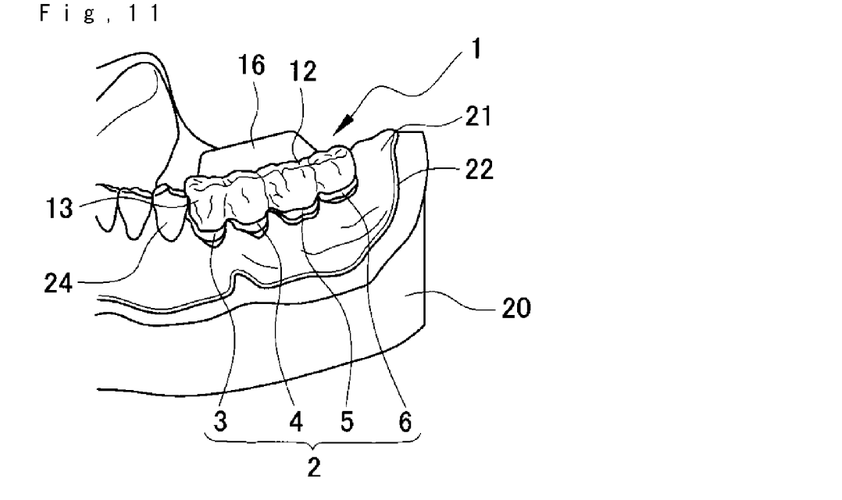
FIG. 11 is a perspective view showing a state of the lower-jaw left artificial molar teeth fixed in the artificial teeth accommodating portion of the artificial teeth packaging container shown in FIG. 1, being mounted on a wax rim.

First, as shown in FIG. 10, a mandible model 20 is fixed to a lower jaw fixing portion 19 of an articulator 18 for simulating the motion of human jaws, and a lower jaw wax rim 21 of horseshoe shape is attached to a lower jaw base plate 22 made of resin. By pressing with a dental instrument heated by electric iron or burner, a bulge portion of the lower jaw wax rim 21 is softened. The lower artificial anterior teeth 23 are buried and arranged in a softened bulge portion of the lower jaw wax rim 21. By using the articulator 18, adjustment of mutual occlusion state of lower artificial anterior teeth 23 is completed, and thereafter, a cervical portion of the lower artificial anterior teeth 23 is fixed by wax or the like.

In this way, after completing adjustment of arrangement and occlusion of the lower artificial anterior teeth 23, the bulge portion of the lower jaw wax rim 21 of a buried portion of the lower left molar teeth 2 is softened by the electric iron or the like. In the softened bulge portion of the lower jaw wax rim 21, the four lower-jaw left artificial molar teeth 2 packaged in the artificial teeth packaging container 1 of the embodiment are buried. At this time, by reference to the slit 14 of the artificial teeth packaging container 1, a positional relation is adjusted between the lower-jaw left artificial first premolar tooth 3 and the adjacent lower-jaw left artificial canine tooth 24, and as shown in FIG. 12, at the same time, by utilizing an occlusal plane plate 25 of the articulator 18 adjusted in parallel to a virtual occlusal plane, a position of the plane plate portion 16 of the artificial teeth packaging container 1 is adjusted so as to be disposed parallel to the virtual occlusal plane. In the same method as mentioned above, a lower-jaw right artificial molar teeth 2' at a right side packaged by an artificial teeth packaging container 1' symmetrical in shape with a shape of the embodiment is buried into the bulge portion of the lower jaw wax rim 21. As shown in FIG. 12, the dentist or dental technician confirms that the plane plate portions 16, 16' or the right and left artificial teeth packaging containers 1, 1' are parallel to the occlusal plane plate 25 of the articulator 18, and determines the arrangement of the right and left lower artificial molar teeth 2, 2', and the cervical portion is fixed by wax or the like. When the wax for fixing the artificial teeth is cured, the right and left artificial teeth packaging containers 1, 1' are removed from the right and left lower artificial molar teeth 2, 2', and the arrangement work of the right and left lower artificial molar teeth 2, 2' is completed.

According to the artificial teeth packaging container 1 of the embodiment, since the four lower-jaw left artificial molar teeth 2 are fixed by the artificial teeth accommodating portion 7 so as to maintain the arrangement position relation with the adjacent artificial teeth and the arrangement position relation with the upper left artificial molar teeth above, the artificial molar teeth 3 to 6 contained in the artificial teeth packaging container 1 of the embodiment are determined in the positional relation capable of exhibiting the characteristics to the maximum, and the four lower-jaw left artificial molar teeth 2 can be arranged in batch, without the trouble of arranging the artificial molar teeth individually.

When the four lower-jaw left artificial molar teeth 2 are arranged in the bulge portion of the lower jaw wax rim 21, the slit 14 is the reference for positioning between the lower-jaw left artificial first premolar tooth 3 and the lower-jaw left artificial canine tooth 24, and the plane plate portion 16 becomes the reference for arrangement of the four lower-jaw left artificial molar teeth 2. By using the slit 14 and plane plate portion 16, when the four lower-jaw left artificial molar teeth 2 are buried in the bulge portion of the lower jaw wax rim 21, it is easy to adjust the arrangement position relation with the adjacent artificial teeth and the arrangement position relation with the upper left artificial molar teeth above.

The artificial teeth packaging container 1 of the embodiment is a mere example for explaining the invention as mentioned above, and the configuration of the artificial teeth accommodating portion 7 is not limited to the explained example, but the artificial teeth accommodating portion 7 may be modified as follows.

The configuration of the artificial teeth accommodating portion 7 is not particularly specified as far as the plurality of artificial teeth arranged consecutively can be fixed detachably, while keeping the arrangement position relation with the adjacent artificial teeth and the arrangement position relation with the upper or lower artificial molar teeth, and the artificial teeth accommodating portion 7 may be designed so as to store and fix a plurality of artificial teeth in a desired combination. For example, four upper artificial molar teeth of either right or left side, a total of fourteen lower and upper artificial teeth, or two, four or six of mutually adjacent upper or lower artificial anterior teeth may be combined as artificial teeth to be accommodated in the artificial teeth accommodating portion 7, and the artificial teeth accommodating portion 7 may be formed so as to fix such combination of artificial teeth detachably.

When the artificial teeth packaging container 1 is designed to package artificial teeth, the through-hole 15 for injection of adhesive agent is formed individually in the wall portion of a cutting edge portion contact surface side.

The artificial teeth packaging container 1 of the embodiment is not limited to a configuration of packaging the mutually separated artificial teeth, but may be designed to package two or four continuously arranged teeth, as mutually connected anterior teeth or connected molar teeth.

Further, in the artificial teeth packaging container 1, the artificial teeth accommodating portion 7 may be formed smaller than artificial teeth so that the artificial teeth may be pressed and fixed into the artificial teeth accommodating portion 7 by musing the elastic force of the artificial teeth packaging container 1.

Figure 13:
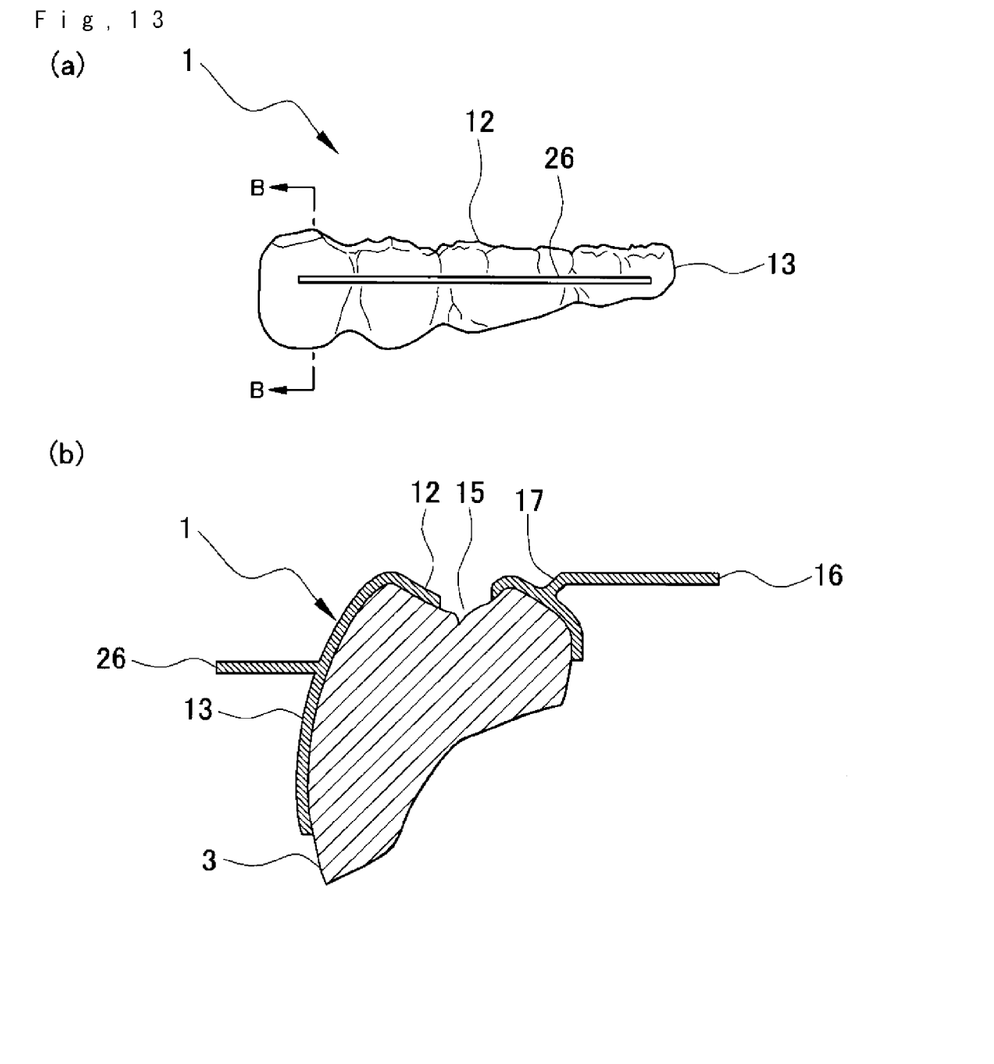

As shown in FIG. 13, a gripping plate 26 for assisting separation may be disposed perpendicularly on an outer surface of the peripheral wall 13 at an opposite side of the plane plate portion 16. When the arrangement operation of artificial teeth is completed, by gripping this gripping plate 26 for assisting separation, the artificial teeth packaging container 1 of the embodiment can be separated from the arranged artificial teeth.

The invention claimed is:

1. A system comprising:
   an artificial teeth packaging container; and
   artificial teeth accommodated in the artificial teeth packaging container, the artificial teeth being a set of non-natural teeth each corresponding to a respective one of a set of natural teeth found in a human jaw;
   wherein the artificial teeth packaging container includes an artificial teeth accommodating portion configured to detachably hold the artificial teeth provided separately from a human body such that said artificial teeth accommodating portion covers an occlusal portion of the artificial teeth from an occlusal plane and exposes a cervical portion of the artificial teeth, the artificial teeth being arranged in said artificial teeth accommodating portion so as to have a positional relationship relative to adjacent artificial teeth and relative to opposing upper or lower artificial teeth, the positional relationship being a prosthetic positional relationship in which alignment of the artificial teeth is based on the set of natural teeth found in the human jaw, said artificial teeth accommodating portion having an occlusal surface contact side wall configured to directly contact a lingual side surface of the artificial teeth and a peripheral wall configured to directly contact a buccal side surface of the artificial teeth,
   wherein the artificial teeth packaging container includes a plane plate portion connected to said occlusal surface contact side wall and extending outwardly from the artificial teeth accommodating portion toward a lingual side, said plane plate portion extending along substantially an entire length of at least two artificial teeth covered by said occlusal surface contact side wall, and
   wherein the artificial teeth are detachably accommodated in the artificial teeth accommodating portion.

2. The system of claim 1, wherein said artificial teeth accommodating portion includes an artificial first premolar tooth accommodating portion, an artificial second premolar tooth accommodating portion, an artificial first molar tooth accommodating portion, and an artificial second molar tooth accommodating portion, and
   wherein said peripheral wall at said artificial first premolar tooth accommodating portion of the artificial accommodating portion has a positioning slit configured to adjust an arrangement position relation between an artificial first premolar tooth and an artificial canine tooth.

3. The system of claim 1, wherein said plane plate portion is disposed in parallel to a virtual occlusal plane.

4. The system of claim 1, wherein the said artificial teeth packaging container is a resin material of about 0.2 mm to 2 mm in thickness, and is selected from polyvinyl chloride, polystyrene, polyethylene terephthalate, polypropylene, or amorphous polyethylene terephthalate.

5. The system of claim 1, wherein said peripheral wall of said artificial teeth accommodating portion is extended from a maximum prominent portion of the artificial teeth toward a cervical portion side, and contacts along said peripheral surface of the artificial teeth.

6. The system of claim 1, wherein a through-hole configured to enable injection of adhesive agent is disposed in said occlusal surface contact side wall in the vicinity of a center of each occlusal surface with the artificial teeth.

7. The system of claim 1, wherein said artificial teeth accommodating portion is configured to enable the artificial teeth to be pressed and fixed in said peripheral wall of said artificial teeth accommodating portion.

8. The system of claim 1, wherein said plane plate portion extends along substantially an entire length of at least three artificial teeth covered by said occlusal surface contact side wall.

* * * * *